United States Patent

Wu et al.

Patent Number: 5,512,189
Date of Patent: Apr. 30, 1996

[54] ANTIWEAR AND ANTIOXIDANT ADDITIVES

[75] Inventors: Shi-Ming Wu, Newtown, Pa.; Andrew G. Horodysky, Cherry Hill, N.J.

[73] Assignee: Mobil Oil Corporation, Fairfax, Va.

[21] Appl. No.: 278,780

[22] Filed: Jul. 22, 1994

Related U.S. Application Data

[63] Continuation-in-part of Ser. No. 24,014, Mar. 2, 1993, abandoned.

[51] Int. Cl.$^6$ .............................. C10M 137/10; C07F 9/17
[52] U.S. Cl. .................................. 252/46.6; 252/389.21; 252/400.21; 558/160; 558/179; 558/182
[58] Field of Search ............................ 252/32.7 E, 46.6, 252/400.21, 389.21; 558/160, 179, 182

[56] References Cited

U.S. PATENT DOCUMENTS

| | | | |
|---|---|---|---|
| 2,559,510 | 7/1951 | Mikeska et al. | 252/56 S |
| 2,559,521 | 7/1951 | Smith, Jr. et al. | 252/56 S |
| 2,564,106 | 8/1951 | Gribbins et al. | 252/400.2 |
| 3,350,348 | 10/1967 | Braid | 558/160 |
| 3,402,224 | 9/1968 | Schicke | 558/160 |
| 3,544,465 | 12/1970 | Braid | 252/46.6 |
| 3,567,638 | 3/1971 | Braid | 252/46.6 |
| 3,654,154 | 4/1972 | Braid | 252/46.6 |
| 3,683,054 | 8/1972 | Wollensak et al. | 252/46.6 |
| 3,755,501 | 8/1973 | Braid | 252/46.6 |
| 4,589,993 | 5/1986 | Cleveland et al. | 252/46.6 |
| 4,834,893 | 5/1989 | Doner et al. | 252/46.6 |
| 5,084,069 | 1/1992 | Farng | 252/46.6 |

OTHER PUBLICATIONS

Hawley's Condensed Chemical Dictionary, (NY, 1987) p. 1149 (No month available).

*Primary Examiner*—Margaret Medley
*Attorney, Agent, or Firm*—Alexander J. McKillop; Malcolm D. Keen; Jessica M. Sinnott

[57] ABSTRACT

A reaction product useful as an antiwear or antioxidant additive in lubricants is made by reacting a sulfur-containing carboxylic acid, i.e. 3,3'-thiodipropionic acid and a phosphorodithioate, i.e. butoxylated bis(2-ethylhexyl) phosphorodithioic acid.

19 Claims, No Drawings

ANTIWEAR AND ANTIOXIDANT ADDITIVES

CROSS-REFERENCE TO RELATED APPLICATIONS

This is a continuation-in-part of U.S. application Ser. No. 08/024,014 filed Mar. 2, 1993 now abandon, which is incorporated herein by reference in its entirety.

FIELD OF THE INVENTION

The invention is directed to an antiwear and antioxidant additive for a lubricant. More specifically, the invention is directed to the reaction product of an organophosphorodithioate and a sulfur-containing carboxylic acid and lubricant compositions containing the reaction product.

BACKGROUND OF THE INVENTION

Direct frictional contact between relatively moving surfaces even in the presence of a lubricant can cause wear of the surfaces. The elimination of wear is an ideal goal which is approached by blending the lubricating media with additives which can reduce the wear. The most suitable antiwear additives are those that help to create and maintain a persistent film of lubricant even under severe conditions which would tend to deplete the lubricant film such as high temperatures which thin the lubricant film and extreme pressures which squeeze the lubricant film away from the contacting surfaces.

Wear is a serious problem in internal combustion engines, diesel engines and gasoline engines in which metal parts are exposed to sliding, rolling and other types of forceful, frictional mechanical contact. Specific areas of wear occur in the gears, particularly hypoid gears which are under high loads, piston rings and cylinders and bearings such as ball, sleeve and roller bearings. Since antiwear lubricants are made by incorporating antiwear additives into the lubricating fluid, compatibility of the additive is important. Compatibility is a problem encountered in the art because the antiwear functionality is usually polar which makes that portion insoluble in the lubricant. It is desirable to make antiwear additives which maintain the antiwear functionality while, at the same time, are soluble in the lubricant fluid.

Rust prevention is important in systems which are made from ferrous alloys, other than stainless steel, which are subject to rusting upon exposure to humid air. Mineral oils notoriously do not have good rust preventative properties and have; therefore, been mixed with appropriate antirust additives. While synthetic oils have better antirust properties they too can benefit from compatible antirust additives. Antirust additives are usually hydrophobic polar compounds which are adsorbed at the metal surface to shield the surface from exposure to corrosive compounds present in the environment. Known antirust additives of this kind include esters of phosphorus acids. Other antirust additives have the ability to neutralize the acidity of the lubricant as oxidation occurs. Antirust additives of this kind which are particularly useful under relatively high temperature conditions are nitrogenous compounds; e.g. alkyl amines and amides.

Oxidation of a lubricating oil occurs during ordinary, as well as severe, conditions and use. The properties of the oil change due to contamination of the oil and chemical changes in the oil molecules. Oxidation can lead to bearing corrosion, ring sticking, lacquer and sludge formation and excessive viscosity. Acid and peroxide oxidation products can promote corrosion of metal parts, particularly in bearings. The presence of an antioxidant can have a profound effect upon the rate of oxidation of the lubricating oil. Known antioxidants include hydroxy compounds, such as phenols, nitrogen compounds such as amines and phosphorothioates, particularly zinc dithiophosphates.

The use of phosphorodithioate compositions, specifically the zinc dithiophosphates have been known as multifunctional antiwear, peroxide decomposing and bearing corrosion inhibiting additives.

Thiodipropionic acid has been described as an antioxidant additive in lubricant applications, see Hawley's *Condensed Chemical Dictionary*, (New York, 1987) at p. 1149.

SUMMARY OF THE INVENTION

The invention is directed to an additive for a lubricant which has demonstrated wear and oxidation inhibiting properties in a lubricant. Additional properties which are expected are load-carrying and antirust activities.

The invention is directed to a reaction product of a sulfur-containing carboxylic acid and an organophosphorodithioate, lubricants containing the reaction product and methods of making the same.

More specifically, the lubricant additive comprises a reaction product of a sulfur-containing carboxylic acid which can be a mono-, di- or polycarboxylic acid and an alkoxylated diorganophosphorodithioate (diorgano- phosphorodithioatealkylene oxide addition product) of the formula:

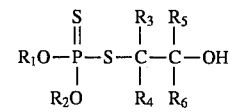

where $R_1$ and $R_2$ are the same or different straight or branched chain hydrocarbyl radicals containing about 1 to 30 carbon atoms, $R_3$, $R_4$, $R_5$ and $R_6$ are each independently a hydrogen atom or a hydrocarbyl radical containing about 1 to 60 carbon atoms, at least one of $R_3$, $R_4$, $R_5$ and $R_6$ is a hydrogen atom.

DETAILED DESCRIPTION OF THE INVENTION

The invention is directed to a reaction product of a sulfur-containing carboxylic acid and an organophosphorodithioate, which exhibits antiwear and antioxidant properties in a lubricant.

The alkoxylated diorgano phosphorodithioate starting material is made in a reaction between phosphorus pentasulfide and an alcohol or phenol to form the diorgano phosphorodithioate which is then reacted with an alkylene oxide or epoxide to form the diorgano phosphorodithioate-derived alcohol (also designated the alkoxylated diorgano phosphorodithioate). The reaction mechanism is believed to follow the following scheme:

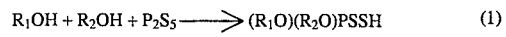

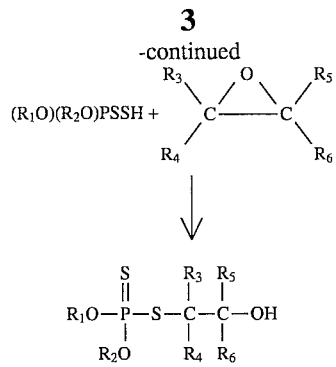

$$(R_1O)(R_2O)PSSH + \underset{R_4}{\overset{R_3}{\diagdown}}C\underset{\phantom{R_6}}{\overset{O}{-\!\!\!-\!\!\!-\!\!\!-}}C\underset{R_6}{\overset{R_5}{\diagup}} \quad (2)$$

$$\underset{\underset{R_2O}{|}}{\overset{\overset{S}{\|}}{R_1O-P-S}}-\underset{\underset{R_4}{|}}{\overset{\overset{R_3}{|}}{C}}-\underset{\underset{R_6}{|}}{\overset{\overset{R_5}{|}}{C}}-OH \quad (3)$$

Where $R_1$ and $R_2$ are the same or different straight or branched chain hydrocarbyl radicals containing 1 to 30 carbon atoms or aromatic hydrocarbyls. $R_3$, $R_4$, $R_5$ and $R_6$ are each independently a hydrogen atom or a hydrocarbyl radical having 1 to 60 carbon atoms, at least one of $R_3$, $R_4$, $R_5$ and $R_6$ is a hydrogen atom. Examples of appropriate alcohols for reacting with the $P_2S_5$ are those in which the hydrocarbyl radical, represented by $R_1$ and $R_2$, are methyl, ethyl, propyl, butyl, pentyl, hexyl, octyl, decyl, dodecyl, octadecyl, eicosyl and branched chain hydrocarbyls such as ethylhexyl, methylpropyl, methylpentyl and mixtures thereof. Specific examples of alcohols include methanol, ethanol, n-propanol, i-propanol, n-butanol, i-butanol, dimethyl butanol, primary and secondary pentanols, hexanol, ethylhexanol, eicosanol and mixtures thereof. Other hydrocarbyl radicals contemplated include 2-butanol (1-methylpropanol), 4-methyl-2-pentanol(1,3-dimethyl-butanol), methylpropyl alcohol which can be a 1-methylpropanol (i.e., 2-butanol) or 2-methylpropanol (i.e. 1-butanol), dimethylbutanol which can be a 1,3-dimethylbutanol (i.e. 4-methyl- 2-pentanol) or 3,3-dimethylbutanol or 2,2-dimethylbutanol or 1,1-dimethylbutanol or 2,3-dimethylbutanol. The $P_2S_5$, as mentioned above, can also be reacted with phenolic compounds such as phenol and alkyl-substituted phenol wherein the alkyl group contains 1 to 30 carbon atoms.

Epoxides which are contemplated for making the starting material include $C_1$ to $C_{60}$ alkylene oxides which contain straight or branched chain or cyclic hydrocarbyl radicals represented by $R_3$, $R_4$, $R_5$ and $R_6$. Representative examples of suitable epoxides include: ethylene oxide, propylene oxide, butylene oxide, pentylene oxide, decylene oxide, dodecylene oxide, hexadecylene oxide, octadecylene oxide, styrene oxide, stilbene oxide and cyclohexene oxide, isomers thereof and mixtures thereof.

The phosphorodithioates can be obtained commercially or they can be made by reacting the alcohol with phosphorus pentasulfide in a ratio of 4 to 1 at an elevated temperature, i.e. a temperature ranging from about 30° to 100° C. (86° F. to 212° F.), preferably from 75° to 95° C. (167° F. to 203° F.). Also, a higher or lower ratio of alcohol to phosphorus pentasulfide can be used. The phosphorodithioates so obtained are then reacted with the epoxides to form the alkoxylated diorgano phosphorodithioate starting materials in equimolar proportions at low temperatures, preferably below about 50° C., ranging from −20° to 50° C.

The organo-phosphorodithioate starting material is reacted with a sulfur-containing carboxylic acid. The sulfur-containing carboxylic acid can be represented by the generic structural formula:

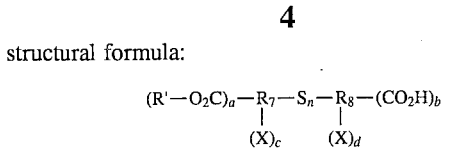

where: n=0–2,
a=0–1,
b=0–1,
c=0–1, and
d=0–1, X is H, SH or $CH_2CO_2H$; provided that when n=0, c+d=1 and X is SH and if n is not 0, then X is not SH, and where R' is hydrogen or a hydrocarbyl radical which contains from about 1 to 60 carbon atoms, more preferably R' is hydrogen or a hydrocarbyl radical containing from 1 to 10 carbon atoms. Representative examples of suitable hydrocarbyl radicals include methyl, ethyl, propyl, butyl, pentyl, hexyl, octyl, decyl, dodecyl, hexadecyl and higher hydrocarbon groups, including isomers thereof such as isobutyl, sec-butyl, tert-butyl, isopentyl and isohexyl. Preferably R' is hydrogen or methyl. $R_7$ and $R_8$ are the same or different hydrocarbyl radical containing 1 to 30 carbon atoms, preferably 1 to 20 carbon atoms. $R_7$ can also be a hydrogen atom. Typically $R_7$ and $R_8$ are straight chain hydrocarbyl radicals and usually $R_7$ is $C_1$ or $C_2$ or $R_7$ is a hydrogen atom. Specific examples of the contemplated sulfur-containing carboxylic acids include 3,3'-thiodipropionic acid, thiodiglycolic acid, thiodisuccinic acid, thioglycolic acid, thiolactic acid, thiomalic acid, dithiodiglycolic acid, dithiodipropionic acid, carbomethoxymercaptosuccinic acid, and the like.

Although not wishing to be bound by it, in one aspect of the invention, the reaction product comprises any one of the following structural formulas:

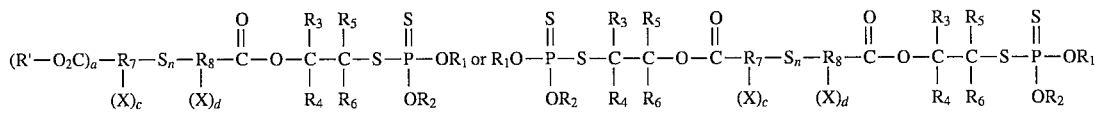

The procedure for m king the reaction product of the invention involves contacting the diorgano phosphorodithioate-alkylene oxide adduct with the sulfur-containing carboxylic acid in proportion expressed in terms of molar ratios ranging from 10:1 to 1:2, preferably 1 to 1 to 2 to 1. An aqueous acid such as sulfuric acid or toluenesulfonic acid in aqueous solution is added to the reaction mixture as a catalyst. The temperature of the reaction mixture is elevated to reflux, i.e. about 0° C. to 250° C. (32° F. to 482° F.), preferably from 100° C. to 200° C. (212° F. to 392° F.) for 5 minutes to 10 hours. The product is then washed and water of reaction is removed under reduced pressure and elevated temperature of about 100° C. to 150° C. (212° F. to 302° F.) to produce the reaction product of the invention.

The sulfur-containing carboxylic acids are commercially available or they can be made by known techniques, for example thioglycolic acid is made by heating chloracetic acid with potassium hydrogen sulfide, thiolactic acid is made by reaction of sodium sulfide, sulfur and bromopropionic acid.

The reaction products are most effective when blended with lubricants in a concentration of about 0.01% to 10%, preferably, from 0.5% to 2% by weight of the total composition.

The contemplated lubricants are liquid oils in the form of either a mineral oil or synthetic oil or mixtures thereof. Also contemplated are greases in which any of the foregoing oils are employed as a base. Still further materials which it is believed would benefit from the reaction products of the present invention are fuels.

In general, the mineral oils, both paraffinic and naphthenic and mixtures thereof can be employed as a lubricating oil or as the grease vehicle. The lubricating oils can be of any suitable lubrication viscosity range, for example, from about 45 SSU at 100° F. to about 6000 SSU at 100° F., and preferably from about 50 to 250 SSU at 210° F. Viscosity indexes from about 70 to 95 being preferred. The average molecular weights of these oils can range from about 250 to about 800.

Where the lubricant is employed as a grease, the lubricant is generally used in an amount sufficient to balance the total grease composition, after accounting for the desired quantity of the thickening agent, and other additive components included in the grease formulation. A wide variety of materials can be employed as thickening or gelling agents. These can include any of the conventional metal salts or soaps, such as calcium, or lithium stearates or hydroxystearates, which are dispersed in the lubricating vehicle in grease-forming quantities in an amount sufficient to impart to the resulting grease composition the desired consistency. Other thickening agents that can be employed in the grease formulation comprise the non-soap thickeners, such as surface-modified clays and silicas, aryl ureas, calcium complexes and similar materials. In general, grease thickeners can be employed which do not melt or dissolve when used at the required temperature within a particular environment; however, in all other respects, any material which is normally employed for thickening or gelling hydrocarbon fluids for forming greases can be used in the present invention.

Where synthetic oils, or synthetic oils employed as the vehicle for the grease are desired in preference to mineral oils, or in mixtures of mineral and synthetic oils, various synthetic oils may be used. Typical synthetic oils include polyisobutylenes, polybutenes, polydecenes, siloxanes and silicones (polysiloxanes).

The lubricating oils and greases contemplated for blending with the reaction product can also contain other additives generally employed in lubricating compositions such as co-corrosion inhibitors, detergents, co-extreme pressure agents, viscosity index improvers, co-friction reducers, co-antiwear agents and the like. Representative of these additives include, but are not limited to phenates, sulfonates, imides, heterocyclic compounds, polymeric acrylates, amines, amides, esters, sulfurized olefins, succinimides, succinate esters, metallic detergents containing calcium or magnesium, arylamines, hindered phenols and the like.

The additives are most effective when used in gear oils. Typical of such oils are automotive spiral-bevel and worm-gear axle oils which operate under extreme pressures, load and temperature conditions, hypoid gear oils operating under both high speed, low-torque and low-speed, high torque conditions.

Industrial lubrication applications which will benefit from the additives include circulation oils and steam turbine oils, gas turbine oils, for both heavy-duty gas turbines and aircraft gas turbines, way lubricants, mist oils and machine tool lubricants. Engine oils are also contemplated such as diesel engine oils, i.e., oils used in marine diesel engines, locomotives, power plants and high speed automotive diesel engines, gasoline burning engines, such as crankcase oils and compressor oils.

Functional fluids also benefit from the present additives. These fluids include automotive fluids such as automatic transmission fluids, power steering fluids and power brake fluids.

It is also desirable to employ the additive in greases, such as, automotive, industrial and aviation greases, and automobile chassis lubricants.

EXAMPLES

The following examples, which were actually conducted, represent a more specific description of the invention.

Example 1—Preparation of Phosphorodithioic Acid

Approximately 520 g of 2-ethyl-1-hexanol was stirred in a reactor equipped with a condenser, thermometer, nitrogen purge inlet and outlet to a caustic trap, to which phosphorus pentasulfide was introduced in portions (5×44.4 g). The reaction temperature was maintained at approximately 90° C. and the contents reacted for six hours. It resulted in 690 g of bis(2-ethylhexyl)phosphorodithioic acid upon filtration.

Example 2—Butoxylated Bis(2-Ethylhexyl)Phosphorodithioic Acid

Under the same reaction conditions generally described in Example 1, approximately 72 g (1.0 mol) of butylene oxide was added in dropwise over a period of about 40 minutes to bis(2-ethylhexyl)phosphorodithioic acid (354 g, 1.0 mol from Example 1) while the reaction temperature was maintained at or below 50° C. The mixture was further stirred for four hours to yield 425 g of S-(2-hydroxybutyl)-O,O-di(2-ethylhexyl)phosphorodithioate.

Example 3

Approximately 35.6 g (0.2 mol) of 3,3'-thiodipropionic acid, 150 ml of toluene and 170.4 g (0.4 mol) of the above product of Example 2 were charged to a four-necked reactor, then 4 ml of 30% sulfuric acid was added to the reaction mixture. The mixture was heated to reflux for eight hours, then washed with water, dried and evaporated under reduced pressure at 130° C. to yield 198 g of grey brown fluid.

EVALUATION OF THE PRODUCTS

Antiwear Properties

The ability of the oil containing the additives of the present invention to prevent the wearing down of metal parts under severe operating conditions was tested in the 4-Ball Wear Test. The results of the test are presented in Table 1. Following the standard ASTM testing procedure, the test was conducted in a device comprising four steel balls, three of which were in contact with each other in one plane in a fixed triangular position in a reservoir containing the test sample. The test sample was an 80% solvent paraffinic bright, 20% solvent paraffinic neutral mineral oil and the same oil containing about 1.0 wt % of the test additive. The fourth ball was above and in contact with the other three. The fourth ball was rotated at 2000 rpm while under an applied load of 60 kg, pressed against the other three balls, the pressure was applied by weight and lever arms. The test was conducted at 200° F. for 30 minutes.

The diameter of the scar on the three lower balls was measured with a low power microscope and the average diameter measured in two directions on each of the three lower balls was taken as a measure of the antiwear characteristics of the test composition. Both tables present data showing the marked decrease in wear scar diameter obtained with respect to the test composition containing the product of the Examples.

TABLE 1

Four-Ball Test
(60 kg load, 2000 rpm, 30 min., 200° F.)

| Item | Wear Scar Diameter (mm) |
| --- | --- |
| Base Oil (80% solvent paraffinic bright, 20% solvent paraffinic neutral mineral oil) | 2.842 |
| 1% Example 3 in above base oil | 0.484 |

The results clearly show good antiwear activity by these post-reaction products.

Antioxidant Properties

The reaction products were blended in a concentration of 1 wt % in a 200 second, solvent refined paraffinic neutral mineral oil and evaluated for antioxidant performance in the Catalytic Oxidation Test at 325° F. for 40 hours. The results are presented in Table 2.

In the Catalytic Oxidation Test a volume of the test lubricant was subjected to a stream of air which was bubbled through the test composition at a rate of about 5 liters per hour for the specified number of hours and at the specified temperature. Present in the test composition were metals frequently found in engines, namely:

1) 15.5 square inches of a sand-blasted iron wire;
2) 0.78 square inches of a polished copper wire;
3) 0.87 square inches of a polished aluminum wire; and
4) 0.107 square inches of a polished lead surface.

The results of the test were presented in terms of change in kinematic viscosity ($\Delta KV$), change in neutralization number ($\Delta TAN$) and the presence of sludge. Essentially, the low $\Delta KV$ meant that the lubricant maintained its resistance to internal oxidative degradation under high temperatures, the low $\Delta TAN$ indicated that the oil maintained its acidity level under oxidizing conditions.

TABLE 2

Catalytic Oxidation Text 40 hours at 325° F.

| Item | Additive Conc. (wt %) | Change in Acid Number $\Delta TAN$ | Percent Change in Viscosity % $\Delta KV$ |
| --- | --- | --- | --- |
| Base oil (200 second, solvent refined, paraffinic neutral, mineral oil) | — | 140.3 | 16.38 |
| Example 3 in above base oil | 1.0 | 29.9 | 2.13 |

As shown above, the products of this invention show very good antioxidant activity as evidenced by control of increase in acidity and viscosity.

What is claimed is:

1. A lubricant composition comprising a major proportion of a lubricant selected from the group consisting of a mineral oil or synthetic oil or blend thereof and a minor multifunctional antiwear and antioxidant amount of a reaction product of an alkoxylated diorgano phosphorodithioate of the formula:

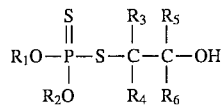

where $R_1$ and $R_2$ are the same or different straight or branched chain hydrocarbyl radicals containing 1 to 30 carbon atoms or aromatic hydrocarbyls, $R_3$, $R_4$, $R_5$ and $R_6$ are each independently a hydrogen atom or a hydrocarbyl radical containing 1 to 60 carbon atoms, at least one of $R_3$, $R_4$, $R_5$ and $R_6$ is a hydrogen atom and a sulfur-containing carboxylic acid having the structural formula:

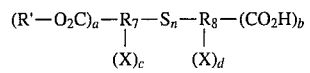

where: n=0–2,
a=0–1,
b=0–1,
c=0–1, and
d=0–1, X is H, SH or $CH_2CO_2H$; provided that when n=0, c+d=1 and X is SH and if n is not 0, then X is not SH, and where R' is hydrogen or a hydrocarbyl radical which contains from about 1 to 60 carbon atoms and $R_7$ and $R_8$ are the same or different hydrocarbyl radicals containing from about 1 to 30 carbon atoms or R7 is a hydrogen atom.

2. The composition of claim 1 in which R' is hydrogen or a hydrocarbyl radical which contains from about 1 to 10 carbon atoms.

3. The composition of claim 1 in which R' is methyl, ethyl, propyl, butyl, pentyl, hexyl, octyl or decyl.

4. The composition of claim 1 in which the sulfur containing carboxylic acid is selected from the group consisting of 3,3'-thiodipropionic acid, thiodiglycolic acid, thiodisuccinic acid, thioglycolic acid, thiolactic acid, thiomalic acid, dithiodiglycolic acid, dithiodipropionic acid and carbomethoxymercaptosuccinic acid.

5. The composition of claim 1 in which the sulfur-containing carboxylic acid is 3,3'-thiodipropionic acid.

6. The composition as described in claim 1 in which $R_1$ and $R_2$ of the alkoxylated diorgano phosphorodithioate is methyl, ethyl, propyl, butyl, pentyl, hexyl, octyl, decyl, dodecyl, octadecyl, eicosyl, ethylhexyl, methylpropyl, methylpentyl and mixtures thereof.

7. The composition as described in claim 1 in which the alkoxylated diorgano phosphorodithioate is derived from a phosphorus pentasulfide, an alcohol or phenol and an alkylene oxide.

8. The composition as described in claim 7 in which the alkylene oxide is ethylene oxide, propylene oxide, butylene oxide, pentylene oxide, decylene oxide, dodecylene oxide, hexadecylene oxide, octadecylene oxide, styrene oxide, stilbene oxide, cyclohexylene oxide, isomers thereof and mixtures thereof.

9. The composition as described in claim 1 in which the lubricant composition is a grease in which the mineral oil or the synthetic oil or the blend thereof is further combined with a thickening agent.

10. The composition as described in claim 1 in which the minor multifunctional amount of the reaction product is 0.01% to 10 wt. % based on the total weight of the lubricant.

11. A lubricant composition comprising a major amount of a lubricant selected from the group consisting of a mineral oil or synthetic oil or blend thereof and a minor multifunctional antiwear and antioxidant amount of a composition having any one of the following structures:

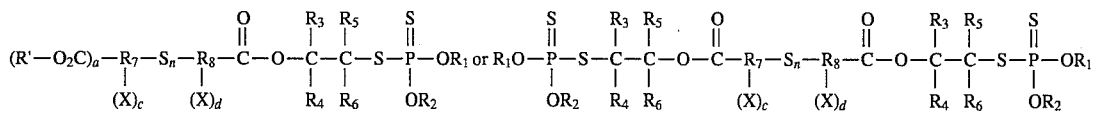

where $R_1$ and $R_2$ are the same or different hydrocarbyl radicals containing 1 to 30 carbon atoms, $R_3$, $R_4$, $R_5$ and $R_6$ are each independently a hydrogen atom or a hydrocarbyl radical containing 1 to 60 carbon atoms, at least one of which is a hydrogen atom, n ranges from 0 to 2, a, b, c and d range from 0 to 1, X is H, SH or $CH_2CO_2H$; provided that when n=0, c+d=1 and X is SH and if n is not 0, then X is not SH, and where R' is hydrogen or a hydrocarbyl radical which contains from about 1 to 60 carbon atoms and $R_7$ and $R_8$ are the same or different hydrocarbyl radicals containing from about 1 to 30 carbon atoms or $R_7$ is a hydrogen atom.

12. A reaction product made by reacting of an alkoxylated diorgano phosphorodithioate of the formula:

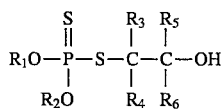

where $R_1$ and $R_2$ are the same or different straight or branched chain hydrocarbyl radicals containing 1 to 30 carbon atoms or aromatic hydrocarbyls, $R_3$, $R_4$, $R_5$ and $R_6$ are each independently a hydrogen atom or a hydrocarbyl radical containing 1 to 60 carbon atoms, at least one of $R_3$, $R_4$, $R_5$ and $R_6$ is a hydrogen atom and a sulfur-containing carboxylic acid having the structural formula:

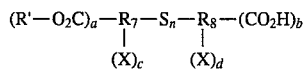

where: n=0–2, a=0–1, b=0–1, c=0–1, and d=0–1, X is H, SH or $CH_2CO_2H$; provided that when n=0, c+d=1 and X is SH and if n is not 0, then X is not SH, and where R' is hydrogen or a hydrocarbyl radical which contains from about 1 to 60 carbon atoms and $R_7$ and $R_8$ are the same or different hydrocarbyl radicals containing from about 1 to 30 carbon atoms or $R_7$ is a hydrogen atom.

13. The reaction product of claim 12 in which R' is a hydrogen atom or a hydrocarbyl radical which contains from about 1 to 10 carbon atoms.

14. The reaction product of claim 12 in which R' is methyl, ethyl, propyl, butyl, pentyl, hexyl, octyl or decyl.

15. The reaction product of claim 12 in which the sulfur containing carboxylic acid is selected from the group consisting of 3,3'-thiodipropionic acid, thiodiglycolic acid, thiodisuccinic acid, thioglycolic acid, thiolactic acid, thiomalic acid, dithiodiglycolic acid, dithiodipropionic acid and carbomethoxymercaptosuccinic acid.

16. The reaction product of claim 12 in which the sulfur-containing carboxylic acid is 3,3'-thiodipropionic acid.

17. The reaction product as described in claim 12 in which $R_1$ and $R_2$ of the alkoxylated diorgano phosphorodithioate is methyl, ethyl, propyl, butyl, pentyl, hexyl, octyl, decyl, dodecyl, octadecyl, eicosyl, ethylhexyl, methylpropyl, methylpentyl and mixtures thereof.

18. The reaction product as described in claim 12 in which the alkoxylated diorgano phosphorodithioate is derived from a phosphorus pentasulfide, an alcohol or phenol and an alkylene oxide.

19. The reaction product as described in claim 12 in which the alkylene oxide is ethylene oxide, propylene oxide, butylene oxide, pentylene oxide, decylene oxide, dodecylene oxide, hexadecylene oxide, octadecylene oxide, styrene oxide, stilbene oxide, cyclohexylene oxide, isomers thereof and mixtures thereof.

* * * * *